(12) United States Patent
Chen et al.

(10) Patent No.: US 7,914,821 B2
(45) Date of Patent: Mar. 29, 2011

(54) PHARMACEUTICAL COMPOSITION FOR PREVENTION AND/OR TREATMENT OF BONE LOSS

(75) Inventors: Chao Hsiang Chen, Tao-Yuan County (TW); Mei-Yin Chien, Tao-Yuan County (TW); Wen-Mei Fu, Taipei (TW); Jin-Ming Chang, Tao-Yuan County (TW)

(73) Assignee: KO DA Pharmaceuticals Co., Ltd., Ping-Cheng, Tao-Yuan County (TW)

( * ) Notice: Subject to any disclaimer, the term of this patent is extended or adjusted under 35 U.S.C. 154(b) by 364 days.

(21) Appl. No.: 12/044,577

(22) Filed: Mar. 7, 2008

(65) Prior Publication Data

US 2009/0226551 A1    Sep. 10, 2009

(51) Int. Cl.
*A61K 35/12* (2006.01)
*A61K 35/32* (2006.01)
*A61K 36/48* (2006.01)
*A61K 36/00* (2006.01)

(52) U.S. Cl. ........ 424/520; 424/549; 424/757; 424/725; 424/777

(58) Field of Classification Search .................. None
See application file for complete search history.

(56) References Cited

U.S. PATENT DOCUMENTS

| 2004/0191344 A1* | 9/2004 | Wang et al. | 424/776 |
| 2005/0233004 A1* | 10/2005 | Shin et al. | 424/549 |
| 2009/0054346 A1* | 2/2009 | Takiguchi et al. | 514/15 |

OTHER PUBLICATIONS

Website document entitled "Buckthorn" from the website http://www.dnr.state.mn.us/invasives/terrestrialplants/woody/buckthorn/index.html, 2 pages. downloaded Jun. 14, 2010.*
Website document entitled "Sea-buckthorn" from the website http://en.wikipedia.org/wiki/Sea-buckthorn, 6 pages, downloaed Jun. 14, 2010.*
Website document entitled "Answers.com—black bean" from the webstie http://www.answers.com/topic/black-bean, 3 pages, downloaded Jun. 14, 2010.*

* cited by examiner

*Primary Examiner* — Christopher R. Tate
(74) *Attorney, Agent, or Firm* — Muncy, Geissler, Olds & Lowe, PLLC

(57) ABSTRACT

A pharmaceutical composition for preventing and/or treating bone loss is disclosed. The pharmaceutical composition includes an effective amount of a licorice, black bean, Cnidi Fructus, and buckhorn.

10 Claims, 21 Drawing Sheets

PHARMACEUTICAL COMPOSITION FOR PREVENTION AND/OR TREATMENT OF BONE LOSS

BACKGROUND OF THE INVENTION

1. Field of the Invention

The present invention relates to a pharmaceutical composition, and in particular relates to a pharmaceutical composition for preventing or treating bone loss.

2. Description of the Related Art

Osteoporosis patients have been divided into two groups including postmenopausal osteoporosis and senile osteoporosis. Postmenopausal osteoporosis generally occurs in older aged women and is caused by female hormone deficiency. Senile osteoporosis generally occurs in older aged men and women. Human bone consists of a hard bone cortex and a soft medullary cavity that contains bone marrow, and the ratio of bone cortex and bone marrow has significant variations at different positions. Postmenopausal osteoporosis usually results in bones mainly consisting of bone marrow, thus leading to fractures, such as lumbar compression fractures and wrist fractures.

Postmenopausal osteoporosis is a metabolic bone disease suffered by older aged women. In clinical research, bone loss reaches up to 3~5% annually for cases with hyposecretion of estrogen for climacteric women. Due to the prolonged lifespan of humans, the incidence trend of postmenopausal osteoporosis has been rising. Additionally, postmenopausal osteoporosis is primarily caused by numerous bone loss due to the deficiency of estrogen (approx. 3-6% or higher every year). In normal state, the excited hormone can stimulate osteoblast to generate cells, which depress the activity of the osteoclast, and stimulate osteoblast to keep the bone in a balanced state. In the absence of estrogen, numerous bones will be lost and calcium ion will be released from the bone, thus inhibiting the concentration of parathyroid hormone and leading to reduced composition of vital vitamins. This will reduce the calcium ion absorbed by the gastrointestinal tract, leading to a calcium ion imbalance, which adds to the rising trend of osteoporosis.

Although postmenopausal osteoporosis may be suppressed by hormone treatment, use of large amounts of hormone over a long period of time may cause serious side effects (Colditz G A, Hankinson S E, Hunter D J. The use of estrogen and progestins and the risk of breast cancer in postmenopausal women. N Eng J Med, 1995, 332:1589-1593; Grady D, Gebretsadik T, Kelikowske K. Hormone replacement therapy and endometrial cancer risk: a meta-analysis. Obstet Gynecol, 1995, 85:304-313). A pharmaceutical composition and method for treating or suppressing bone loss are thus required.

BRIEF SUMMARY OF INVENTION

The present invention provides a method for preventing, ameliorating, and/or treating bone loss, comprising administering to a subject an effective amount of a pharmaceutical composition comprising licorice, black bean, Cnidi Fructus, and buckhorn, wherein a weight ratio of licorice, black bean, Cnidi Fructus, and buckhorn is about 1-10:2-10:1-10:1-10.

The present invention further provides a method for preventing, ameliorating, and/or treating bone loss, comprising administering to a subject an effective amount of a pharmaceutical composition comprising imperatorin and a pharmaceutically acceptable carrier or excipient.

The present invention further provides a method for preventing, ameliorating, and/or treating bone loss, comprising administering to a subject an effective amount of a pharmaceutical composition comprising bergapten and a pharmaceutically acceptable carrier or excipient.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

Figure 1:
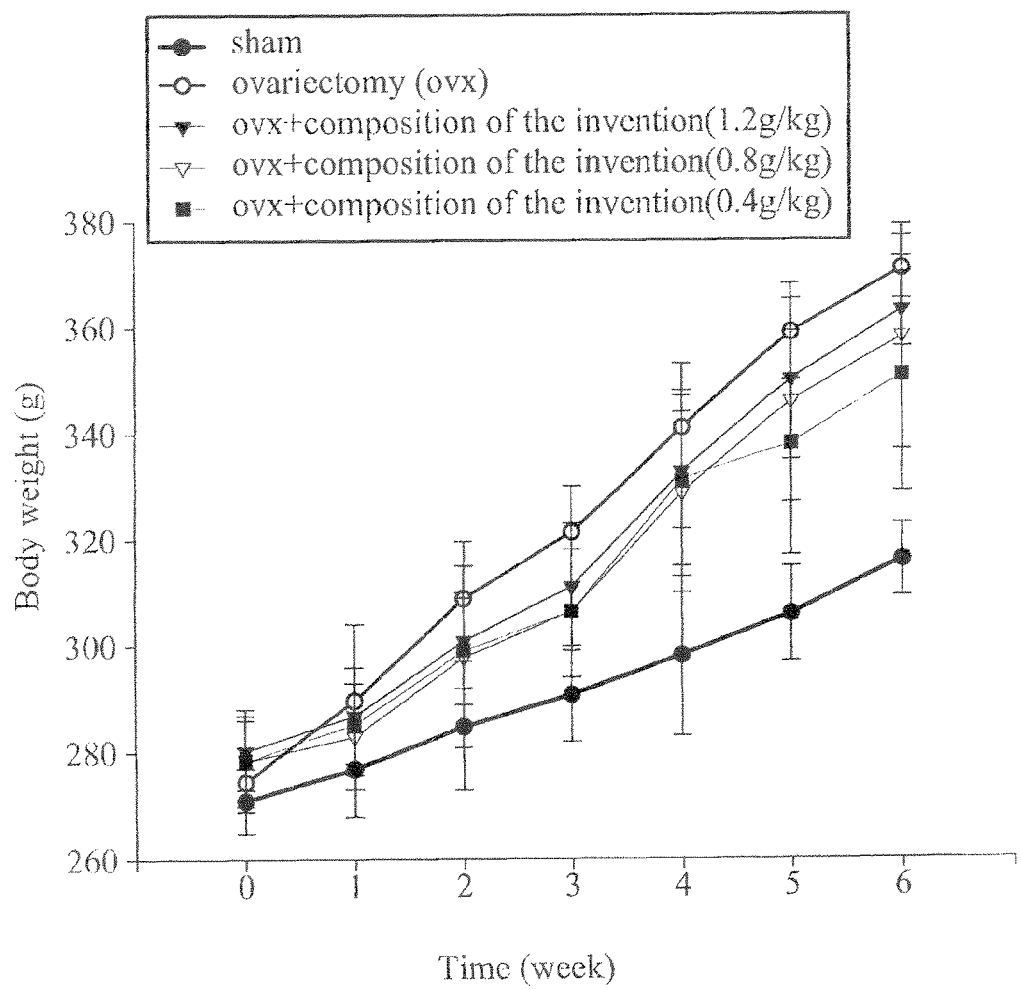
FIG. 1 shows the effect of the pharmaceutical composition of the invention on body weight of rats.

The following description is of the best-contemplated mode of carrying out the invention. This description is made for the purpose of illustrating the general principles of the invention and should not be taken in a limiting sense. The scope of the invention is best determined by reference to the appended claims.

The present invention provides a pharmaceutical composition for preventing, ameliorating and/or treating bone loss, comprising an effective amount of licorice, black bean, Cnidi Fructus, and buckhorn, wherein a weight ratio of licorice, black bean, Cnidi Fructus, and buckhorn is about 1-10:2-10:1-10:1-10, preferably, about 2-4:4-6:1-3:1-3. The pharmaceutical composition also contains osthol, imperatorin, and/or bergapten.

The pharmaceutical composition of the invention can be manufactured using a method as follows. Firstly, licorice is heated and extracted with an extract solution to obtain a licorice extract, wherein the extract solution includes, but is not limited to, water or ethanol. Black bean and Cnidi Fructus are soaked in ethanol for 2 to 40 hours, preferably, 10 to 20 hours, and then extracted using high-temperature heat. Subsequently, the extracted licorice, black bean, and Cnidi Fructus are combined, and the volume ratio of licorice and black bean+Cnidi Fructus is 1:2. The combined extract is concentrated under reduced pressure to give a concentrate (10 to 100 liter). The concentrate is mixed with 10 to 40 kg of buckhorn powder, dried, and formed to obtain the pharmaceutical composition of the invention.

The pharmaceutical composition of the invention can treat, prevent, reduce, or ameliorate bone loss including osteoporosis or an osteoporotic fracture. All bone mineral density (BMD), bone mineral content (BMC), and alkaline phosphatase (ALP) activity of a subject are increased by the pharmaceutical composition. The BMD, BMC, and ALP activity can be increased by at least 5.15%, 3.77%, and 30.0%, preferably, 10.30%, 11.32%, and 90.0%, respectively. Additionally, maximal load, ultimate loading, Young's modulus, and ultimate stress of a bone tissue in a subject also are increased by the pharmaceutical composition. The maximal load, ultimate loading, Young's modulus, and ultimate stress can be increased by at least 3.14%, 5.23%, 7.49%, and 15.65%, preferably, 10.24%, 13.2%, 10.1%, and 34.8%, respectively.

In one embodiment, the pharmaceutical composition comprises an effective amount of imperatorin, and a pharmaceutically acceptable carrier or excipient. The composition may be administered orally or by injection. Following the treatment with the composition containing imperatorin, bone mineral density, bone mineral content, and alkaline phosphatase (ALP) activity of a subject can be increased by at least 12.22%, 28.91%, and 6.0%, respectively. Preferably, the alkaline phosphatase (ALP) activity can be increased by at least 95%. Additionally, the collagen content and mineralization can also be increased by at least 102.0% and 110.0%, respectively.

In another embodiment, the pharmaceutical composition comprises an effective amount of bergapten, and a pharmaceutically acceptable carrier or excipient. The composition may be administered orally or by injection. Following the treatment of the composition containing bergapten, bone mineral density, bone mineral content, and alkaline phosphatase (ALP), activity of a subject can be increased by at least 12.2%, 33.7%, and 80.0%, respectively, and the collagen synthesis and mineralization can be increased by at least 100%, and 105.0%, respectively.

The term "subject", as used herein, means an animal, including a human or non-human mammal, e.g., a dog, a cat, a mouse, a rat, a cow, a sheep, a pig, a goat, or a non-human primate, and expressly includes laboratory mammals, livestock, and domestic mammals. In one embodiment, the mammal may be a human, such as an osteoporosis patient; in another, the mammal may be a rodent, such as a mouse or a rat.

The pharmaceutical composition of the invention may be administered by any Suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection etc.) containing a compound of the invention as an active ingredient, which is suitable for the selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like.

EXAMPLE

Example 1

Manufacturing of the Pharmaceutical Composition of the Invention

The pharmaceutical composition was made up as follows: 30 kg of licorice, 60 kg of black bean, 10 kg of Cnidi Fructus, and 8 kg of buckhorn. The licorice was heated to 100° C., and then extracted with water to give an extract (150 liter). Black bean and Cnidi Fructus were soaked in 30% ethanol for 20 hr at 80° C., and combined with the extract of licorice, wherein the volume ratio of licorice and black bean+Cnidi Fructus was 1:2. The combined extract was concentrated under reduced pressure to give a concentrate (30 liter). The concentrate was mixed with buckhorn powder, dried at 60° C. for 48 hours, and formed to obtain the pharmaceutical composition of the invention.

Example 2

Preparation of Bone Tissue

Eight week old female Sprague-Dawley (SD) rats were purchased from the animal center of the National Laboratory Animal Breeding and Research Center of the National Science Commission. Each rat was caged alone and allowed feedstuff and drinking water for 4 weeks before experimentation. The rats were classified into three groups: (1) sham group, (2) ovariectomy (OVX) group, and (3) OVX+pharmaceutical composition of the invention group. In groups (2) and (3), the rats were anesthetized with trichloroacetaldehyde (400 mg/kg) in a sterile operating environment, whereby access was given to the back of the rat's abdominal cavity from the split lumbar, and the ovaries of both sides of the rat's were fully removed. No ovariectomy was required for group (1) (sham group) with only surgical stitching. The feedstuff and drinking water were taken similarly as before. One day after ovariectomy, the rats were treated with the pharmaceutical composition of the invention (1.2 g/kg) by oral administration everyday in group (3). In groups (1) and (2), the rats were treated with carboxymethyl cellulose. The dosage was modified weekly for six weeks according to the body weight, and then all rats were slaughtered.

Example 3

Measurement of Bone Length and Weight

Figure 2:
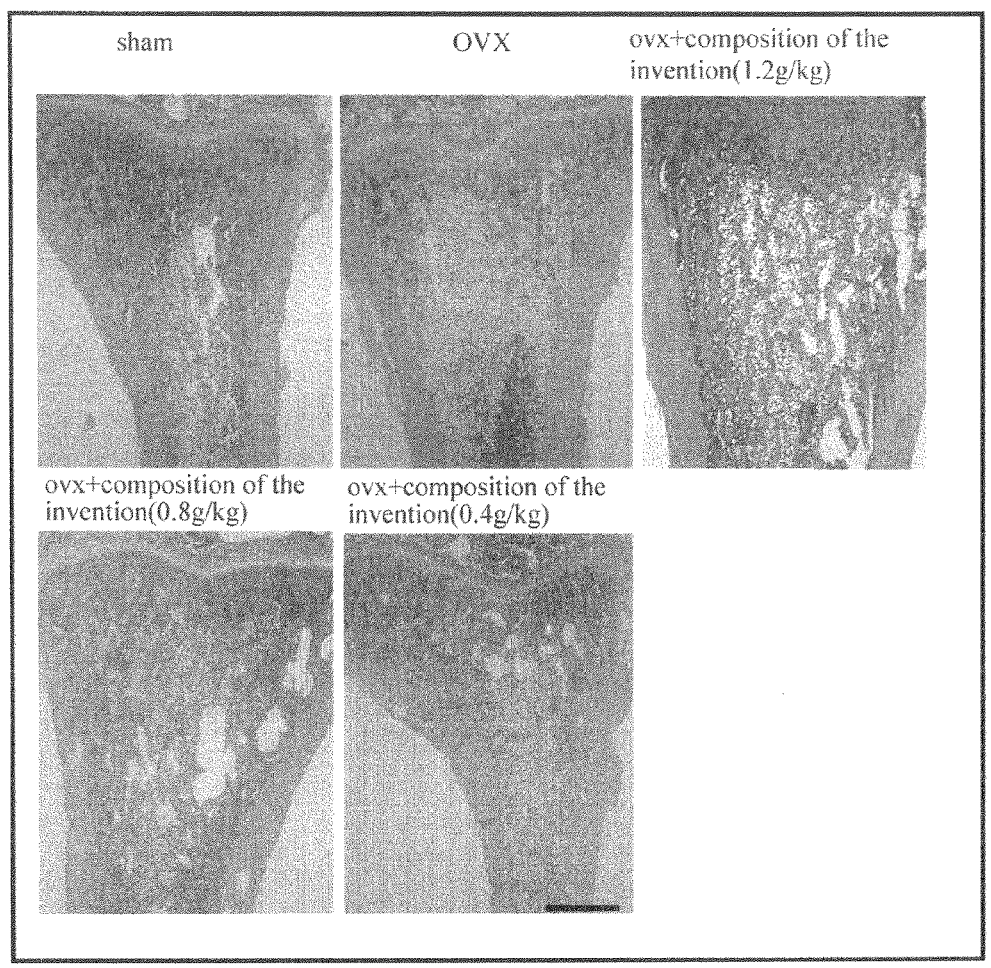
FIG. 2 is a photomicrograph showing the bone tissue of the rats treated with the pharmaceutical composition of the invention.

Rat femur and tibia were isolated from the rats after being slaughtered and kept at −80° C. The muscles and connective tissues were removed from the femurs and tibias. Then, the bone weight was measured by a microblancer, and bone length was measured by a micro scale (±0.05 mm). Bone mineral density (BMD) and content (BMC) were measured using a dual-energy X-ray absorptiometer (DEXA, XR-26; Norland, Fort Atkinson, Wis.). Additionally, the femurs were fixed in 4% formalin for two days, and then treated with 10% EDTA at 4° C. for two weeks of decalcification. After the treatment, the femurs were dehydrated by alcohol, buried into olefin for 5 mm slicing, and stained with Mayer's hematoxylin-eosin. The bone volume of secondary spongiosa was measured by using an image-pro plus (3.0 ed). Referring to FIG. 1, the bone weight of the OVX group rats were heavier than that of the sham group rats, and the pharmaceutical composition did not cause a decrease in body weight of the rats. Referring to FIG. 2, the tissue sections demonstrated that the pharmaceutical composition of the invention suppressed bone loss. The experimental results are listed in Table 1.

TABLE 1

|  | Sham (n = 26) | OVX (n = 26) | OVX + I (1.2 g/kg) (n = 14) | OVX + I (0.8 g/kg) (n = 13) | OVX + I (0.4 g/kg) (n = 13) |
|---|---|---|---|---|---|
| Bone length (mm) | | | | | |
| Tibia | 4.03 ± 0.02 | 4.02 ± 0.02 | 4.04 ± 0.03 | 3.99 ± 0.02 | 4.03 ± 0.0.1 |
| Femur | 3.62 ± 0.04 | 3.65 ± 0.05 | 3.67 ± 0.0.5 | 3.62 ± 0.04 | 3.62 ± 0.03 |
| Wet weight (mg) | | | | | |
| Tibia | 758 ± 10.5 | 657 ± 12.7* | 722 ± 10.6[#] | 716.8 ± 7.4[#] | 693.3 ± 17.1[#] |
| Femur | 958.1 ± 10.3 | 862 ± 13.9* | 911.5 ± 9.6[#] | 923 ± 25.4[#] | 895 ± 15.5[#] |
| BMD (g/cm3) | | | | | |
| Tibia | 0.109 ± 0.009 | 0.097 ± 0.011* | 0.107 ± 0.01[#] | 0.102 ± 0.006 | 0.105 ± 0.006 |
| Femur | 0.131 ± 0.007 | 0.122 ± 0.008* | 0.127 ± 0.011[#] | 0.128 ± 0.028[#] | 0.127 ± 0.016[#] |
| BMC (g) | | | | | |
| Tibia | 0.299 ± 0.012 | 0.265 ± 0.014* | 0.295 ± 0.024[#] | 0.290 ± 0.002[#] | 0.275 ± 0.003[#] |
| Femur | 0.411 ± 0.014 | 0.357 ± 0.013* | 0.402 ± 0.022[#] | 0.415 ± 0.025[#] | 0.408 ± 0.014[#] |
| Bone volume (%) | 17.8 ± 1.6 | 9.3 ± 1.5* | 15.7 ± 1.5[#] | 14.9 ± 1.9[#] | 13.4 ± 2.5[#] |

OVX: ovariectomy
I: the pharmaceutical composition of the invention
*p < 0.05, compared with the sham group
[#]p < 0.05, compared with the OVX group

Example 4

Biomechanics Analysis of Bone Tissue

Biomechanics analysis was dependent upon the measurement of a three-point test by a material testing system (MTS-858, MTS System Inc., Minneapolis, Minn.). The distance from both sides of a bone was 20 mm, and filling speed was 1 mm/m. Young's modulus was obtained by acquiring the regression line of the speed and pressure and substituting both into the following formulas. $\sigma = FLc/4I$, $E = F/d'L/48I$. Wherein, $\sigma$ is ultimate stress, c is the distance from the center of mass (equal to ½b as described above), F is the applied load (N), d is the displacement (mm), and L is the span between the two support points of the bending fixture (mm).

TABLE 2

|  | Sham (n = 26) | OVX (n = 26) | OVX + I (1.2 g/kg) (n = 14) | OVX + I (0.8 g/kg) (n = 13) | OVX + I (0.4 g/kg) (n = 13) |
|---|---|---|---|---|---|
| Maximal load (N) | 102.7 ± 2.9 | 85.9 ± 3.0* | 94.7 ± 2.8[#] | 91.7 ± 2.9[#] | 88.6 ± 1.5 |
| Ultimate loading (N) | 81 ± 4.6 | 70.7 ± 3.8* | 80 ± 2.4[#] | 76.1 ± 2.3[#] | 74.4 ± 1.8 |
| Young's modulus (GPa) | 201 ± 6.2 | 170.8 ± 6.6* | 188 ± 6.8[#] | 187.5 ± 5.9[#] | 183.6 ± 4.2[#] |
| Ultimate stress (MPa) | 18.1 ± 0.9 | 11.5 ± 1.5* | 15.5 ± 1.0[#] | 15.8 ± 1.2[#] | 13.3 ± 1.4[#] |

OVX: ovariectomy
I: the pharmaceutical composition of the invention
*p < 0.05: compared with the sham group
[#]p < 0.05: compared with the OVX group

Example 5

Culture of Rat Osteoblast

Rat primary osteoblast was isolated from the parietal bone of gestation day 18 embryos of Sprague-Dawley rats. After being slaughtered, the embryo rats were obtained from the uteruses of the rats, and calvarium was isolated from the embryo rats. Parietal bone was cut from the calvarium and digested by 0.1% collagenase for 20 minutes to release the bone cells from the bone tissue. The digestion step was repeated five times. The collected bone cells were cultured in α-MEM containing 1% penicillin-streptomycin and 10% FBS in a humidified atmosphere of 5 percent carbon dioxide. When cells were attached and confluence, they were subcultured, which was called "passage 2 (P2)". The passage was for analogizing. 2 to 5 passage cells were used for the experiments.

Example 6

Effect of Each Component on Cell Proliferation

Figure 3A:
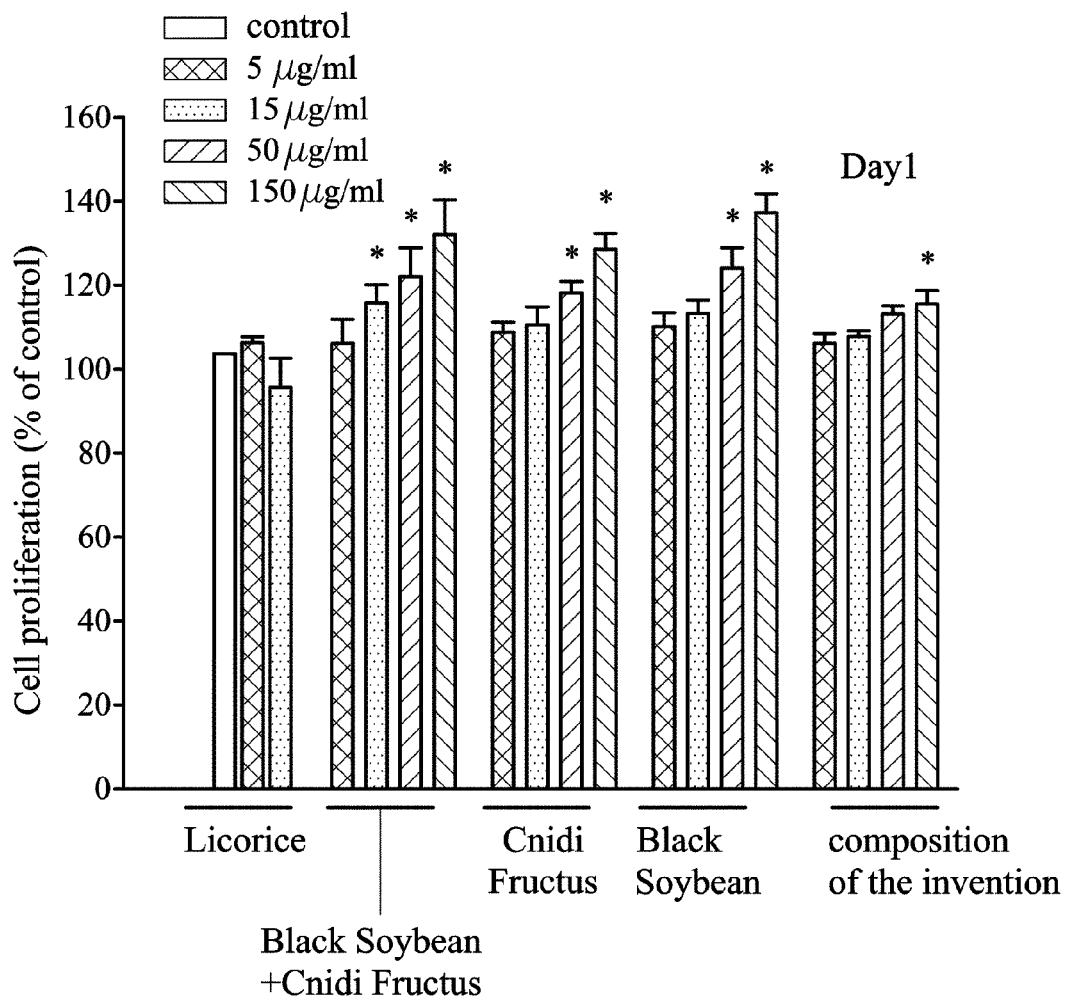
FIG. 3 shows the effect of the pharmaceutical composition of the invention on cell proliferation.
Figure 3B:
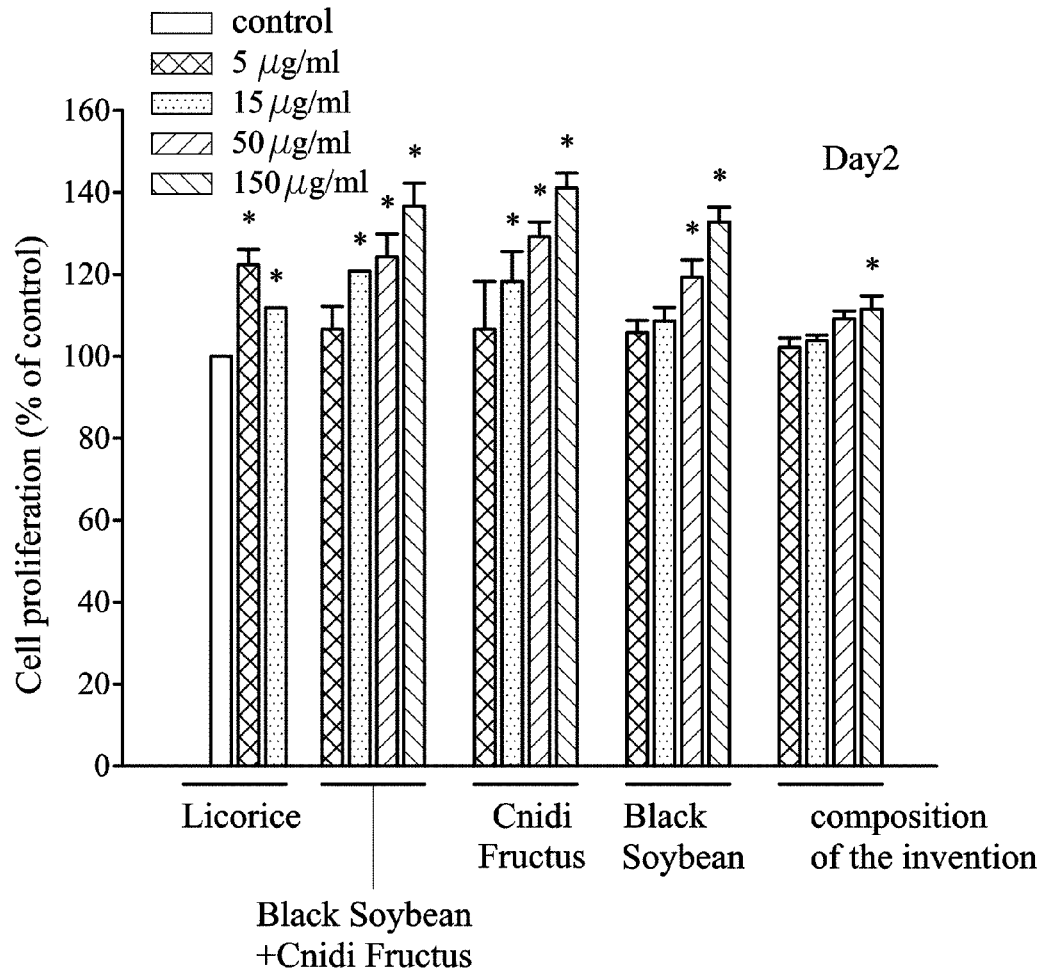

Rat osteoblast cells were isolated and cultured in 96-well Plate according to the methods described above. The osteoblase cells were treated with 5, 15, 50, and 100 μg/ml of (1) licorice, (2) black bean+Cnidi Fructus, (3) Cnidi Fructus, (4) black bean, and (5) the pharmaceutical of the invention for 48 hrs, respectively and then the medium was removed. Proliferation of the osteoblast cells was tested using Cell Proliferation ELISA, BrrdU kit (Roche Applied Science). The proliferation level in the control group which was treated with 0.1% DMSO was defined as 100%. Referring to FIGS. 3A-3B, when compared with the control group, all components increased the proliferation of the osteoblast cells.

Example 7

Effect of Each Component on Alkaline Phosphatase (ALP) Activity

Figure 4:
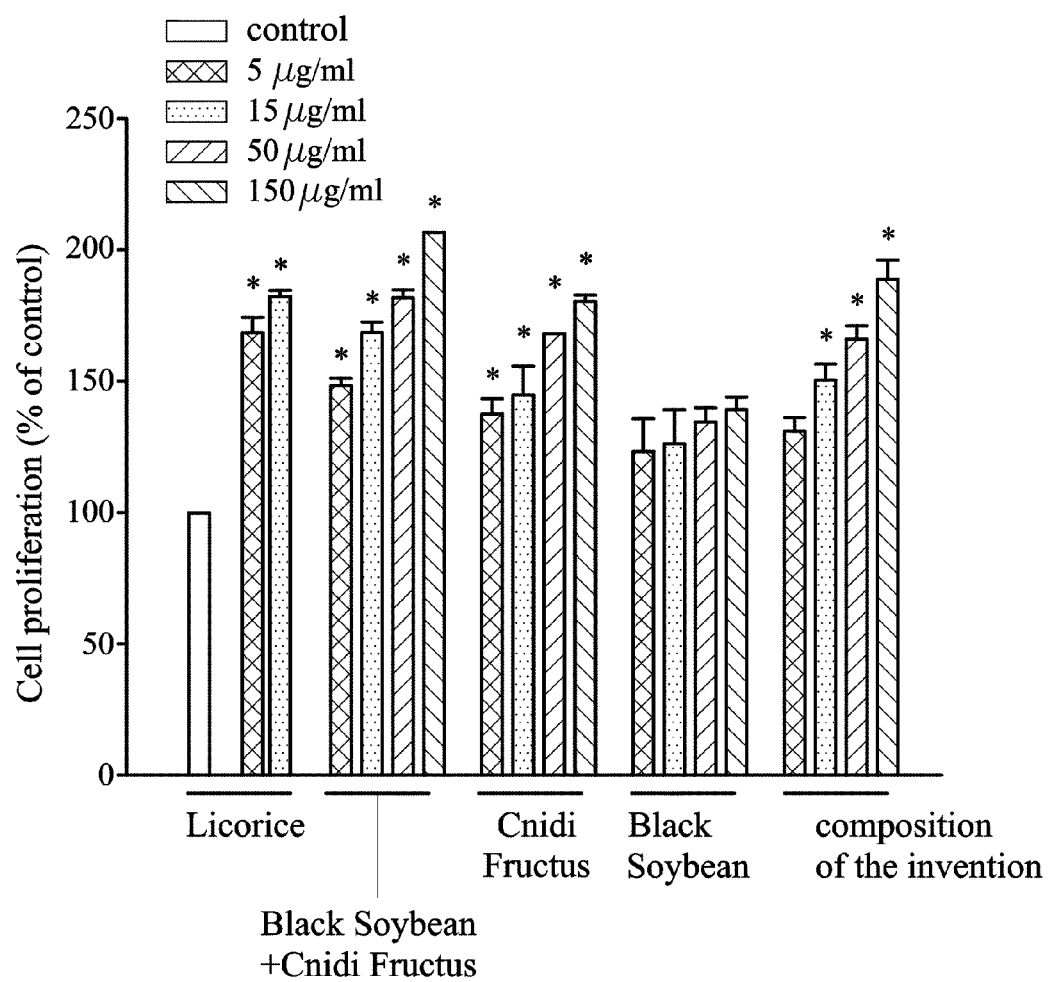
FIG. 4 shows the effect of the pharmaceutical composition of the invention on ALP activity in the bone cells.

Rat osteoblast cells were isolated and cultured in 96-well Plate according to the methods described above. The osteoblast cells were treated with 5, 15, 50, and 100 µg/ml of (1) licorice, (2) black bean+Cnidi Fructus, (3) Cnidi Fructus, (4) black bean, and the pharmaceutical of the invention extract, respectively. The treated osteoblast cells were digested in 0.2% NP-40 solution, and then centrifuged at 1500×g for 5 minutes to obtain a supernatant. The supernatant was analyzed to obtain the ALP activity of the osteoblast cells using an ALP kit (Roche Applied Science). The ALP activity level in the control group which was treated with 0.1% DMSO was defined as 100%. Referring to FIG. 4, all treatments except those treated by the black bean increased the ALP activity of the osteoblast cells.

Example 8

Effect of Each Component on Bone Mineralization

Figure 5A:
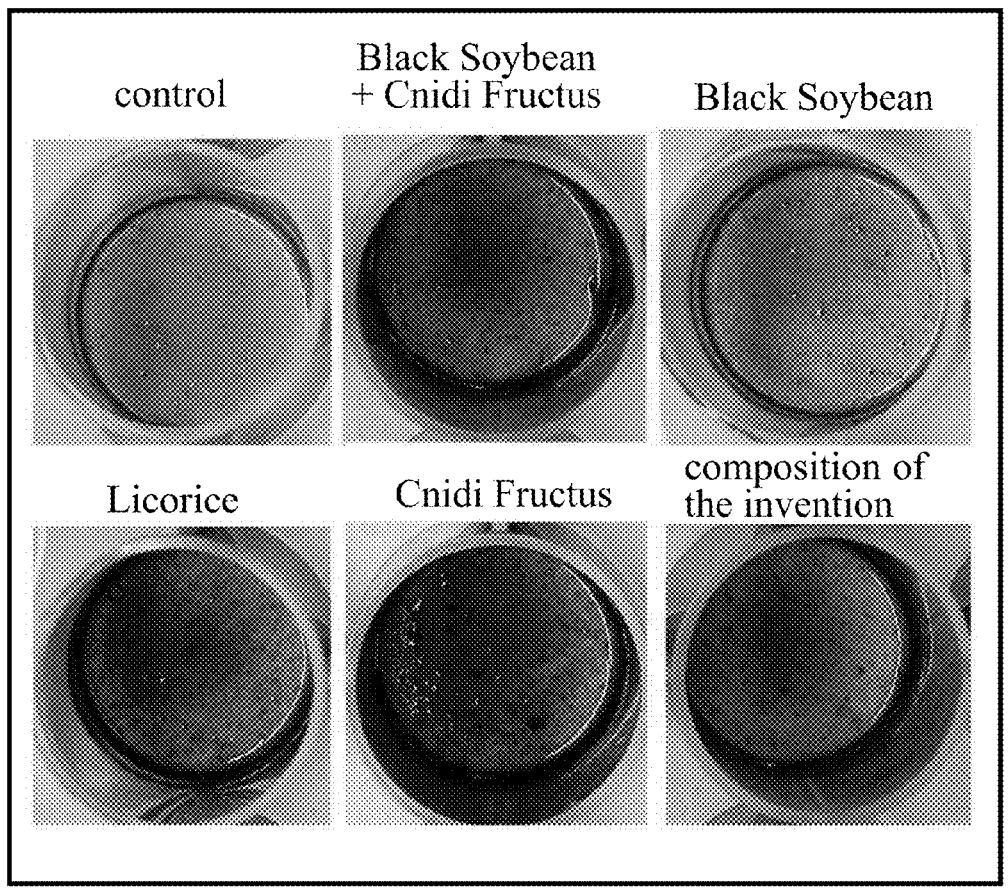
FIGS. 5A-5B shows the effect of the pharmaceutical composition of the invention on bone mineralization.
Figure 5B:
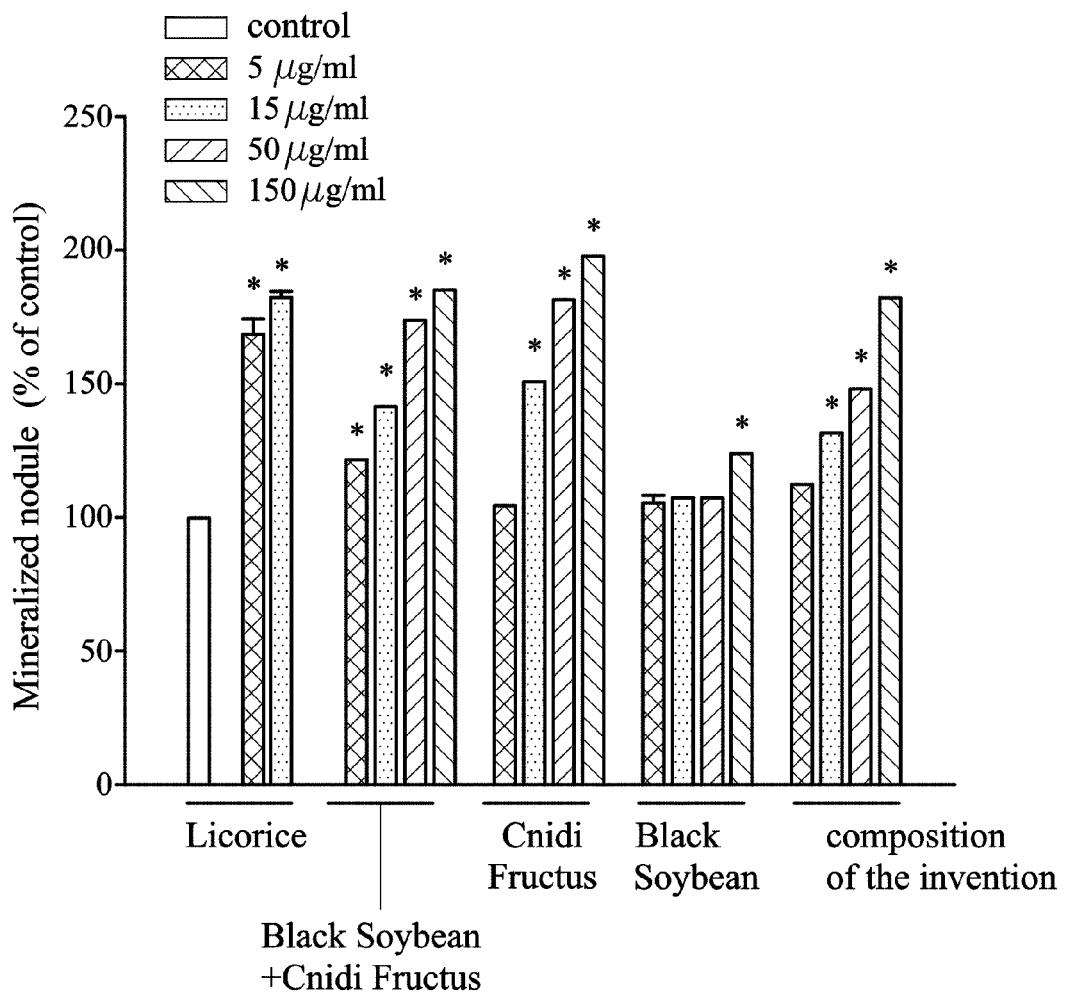

Rat osteoblast cells were cultured in 96-well Plate containing a differentiation medium (5 µg/ml vitamin C and 10 mM β-glycerophosphate) and treated with 5, 15, 50, and 100 µg/ml of (1) licorice, (2) black bean+Cnidi Fructus, (3) Cnidi Fructus, (4) black bean, and (5) the pharmaceutical of the invention, respectively. The differentiation medium was refreshed every 3 days. 14 days after the cell culture, the osteoblast cells were fixed with 75% ethanol for 30 minutes, and then treated with 40 mM Alizarin red-S at room temperature for 1 hr. After the addition of Alizarin red-S, 10% cetylpyridinium chloride was added, and then absorbance was measured at 550 mm. The mineralization level in the control group which was treated with 0.1% DMSO was defined as 100%. Referring to FIGS. 5A-5B, all treatments except those treated by black bean increased the mineralization of the osteoblast cells.

Example 9

Effect of Each Component on Differentiation of the Osteoclast Cells

Figure 6A:
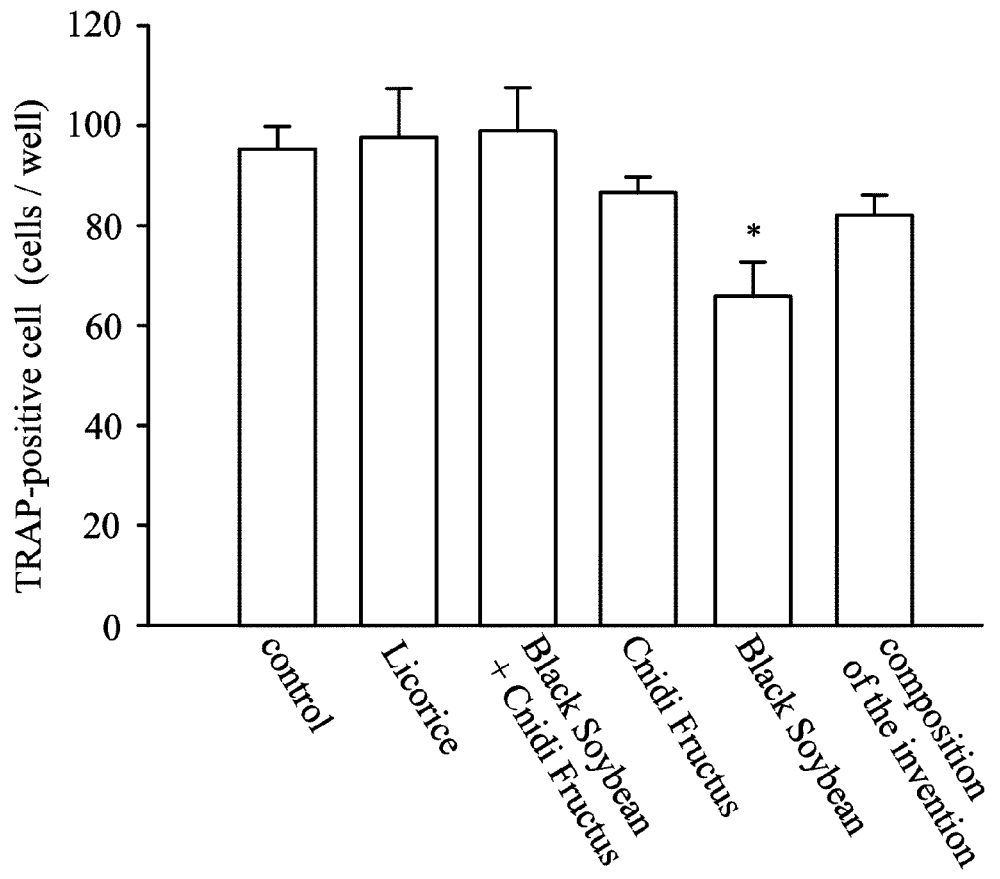
FIG. 6A show the effect of the pharmaceutical composition of the invention on bone cell differentiation.

Rat osteoclast cells were isolated from the bone marrow of Sprague Dawley (SD) rats by a needle. $1 \times 10^6$ osteoclast cells were cultured in a plate with a medium containing a differentiation-inducing agent (50 ng/ml PANKL and 20 µg/in 1 M-CSF), wherein the differentiation-inducing agent was refreshed every 3 days. The cells were treated with 150 µg/ml of (1) licorice, (2) black bean+Cnidi Fructus, (3) Cnidi Fructus, (4) black bean, and (5) pharmaceutical of the invention extract, respectively. Eight days after the cell culture, the cells were stained with tartrate-resistant acid phosphatats (TRAP), and then the TRAP-stained cells (TRAP-positive cell) were measured using a microscope. In the control group, the osteoclast cells were treated with 0.1% DMSO. Referring to FIG. 6A, the differentiation of the osteoclast cells was only slightly suppressed by black bean.

Example 10

Effect of Each Component on Resorption of the Osteoclast Cells

Figure 6B:
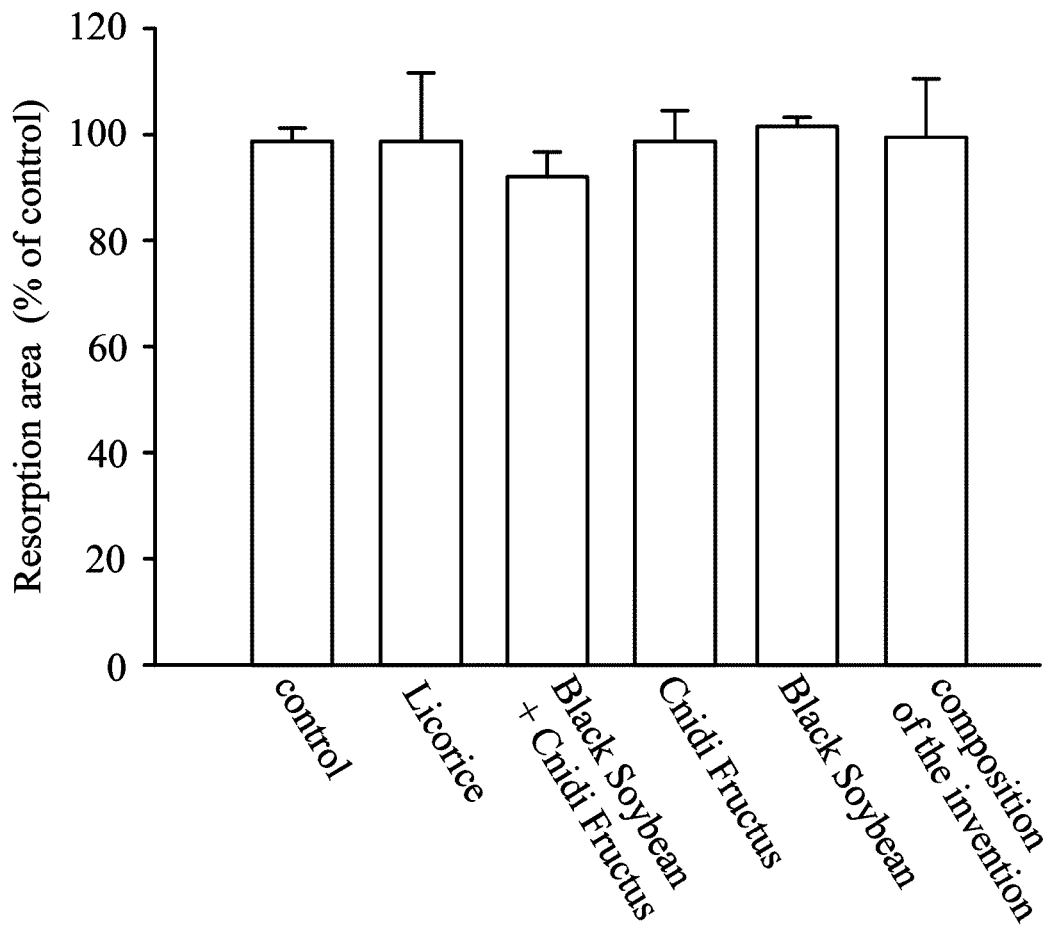
FIG. 6B shows the effect of the pharmaceutical composition of the invention on bone resorption.

Rabbit osteoclast cells were isolated from the long bones of New Zealand White Rabbits (age 5 days) and cultured in OAAS plate. The osteoclast cells were treated with 150 µg/ml of (1) licorice, (2) black bean+Cnidi Fructus, (3) Cnidi Fructus, (4) black bean, and (5) pharmaceutical of the invention extract, respectively. Three days after treatment, the cells were digested with 1 N NaOH, and then washed three times. Following the wash, the cells were photographed under a microscope and analyzed to obtain the resorption area of the osteoclast cells using the Image-Pro Plus 3.0 software. In the control group, the osteoclast cells were treated with 0.1% DMSO. Referring to FIG. 6B, the resorption of the osteoclast cells was not suppressed by all components.

Example 11

Effect of Imperatorin and Bergapten on Cell Viability

Figure 7A:
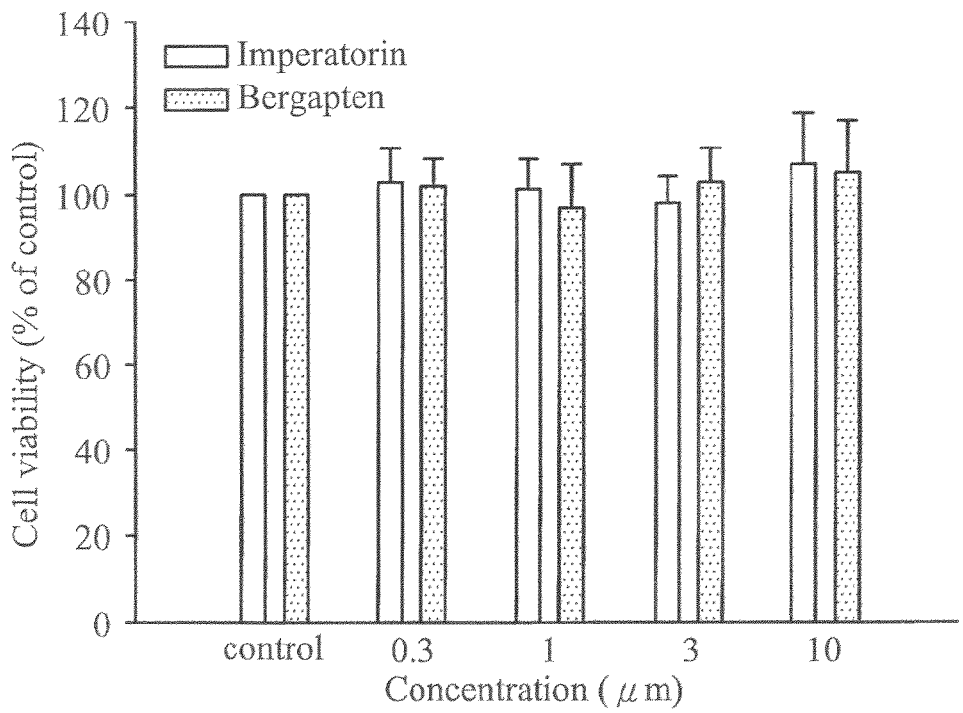
FIG. 7A shows the effect of imperatorin and bergapten on cell viability.

Bone cells were cultured in 96-well plate and treated with 0.3, 1, 3, and 10 µM of imperatorin and bergapten for 48 hrs, respectively. After treatment, the cells were reacted with MTT solution (0.5 mg/ml) at 37° C. for 30 minutes, lysed in 100 µl DMSO, and then absorbance was measured at 550 mm. The cell viability in the control group which was treated with 0.1% DMSO was defined as 100%. Referring to FIG. 7A, both imperatorin and bergapten did not suppress the cell viability.

Example 12

Effect of Imperatorin and Bergapten on Proliferation of Bone Cells

Figure 7B:
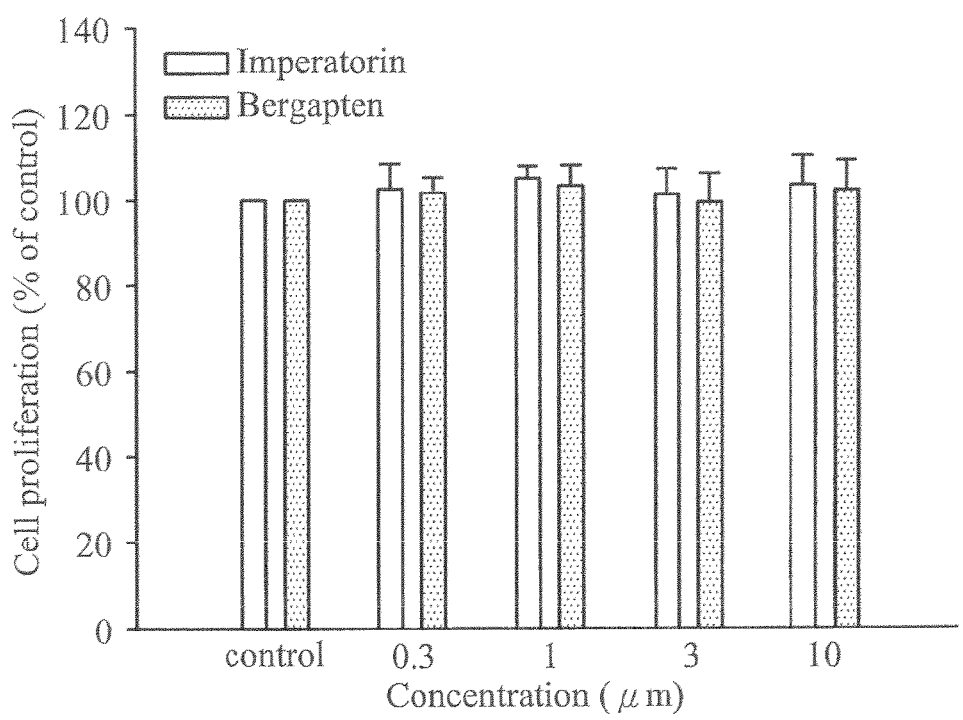
FIG. 7B shows the effect of imperatorin and bergapten on cell proliferation.

Bone cells were cultured in 96-well Plate and treated with 0.3, 1, 3, and 10 µM of imperatorin and bergapten. After treatment, the medium was removed. The proliferation of the bone cells was tested using Cell Proliferation ELISA, BrrdU kit (Roche Applied Science). The proliferation level in the control group which was treated with 0.1% DMSO was defined as 100%. Referring to FIG. 7B, both imperatorin and bergapten were not suppressed the proliferation of the bone cells.

Example 13

Effect of Imperatorin and Bergapten on ALP Activity of Bone Cells

Figure 8A:
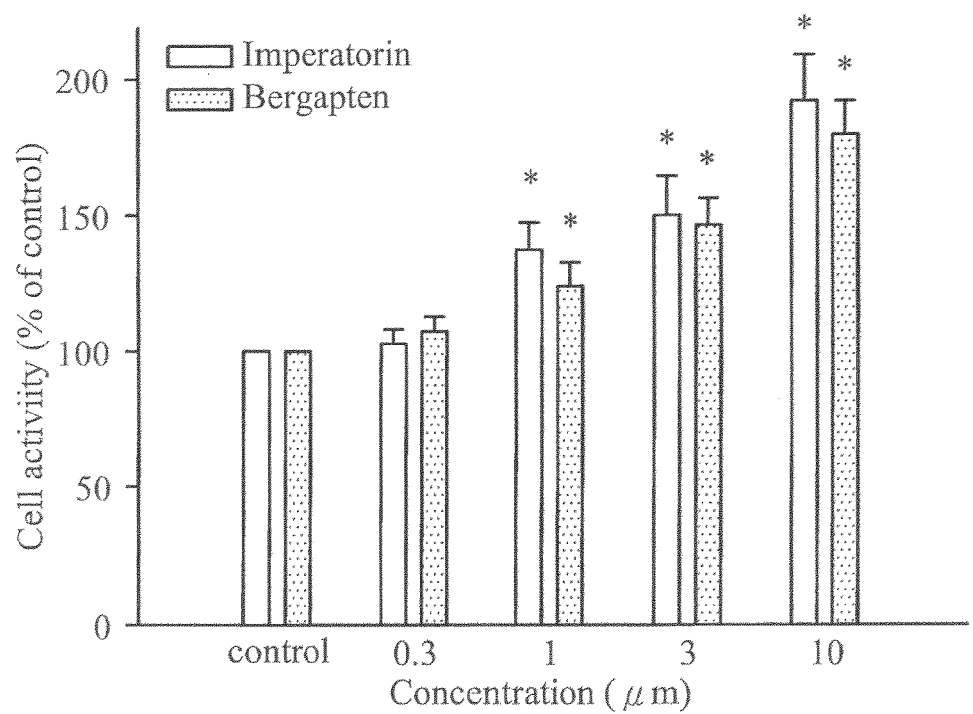
FIG. 8A shows the effect of imperatorin and bergapten on ALP activity in the bone cells.

Bone cells were treated with 0.3, 1, 3, and 10 µM of imperatorin and bergapten, respectively. After treatment, the osteoblast cells were digested in 0.2% NP-40 solution, and then centrifuged at 1500 g for 5 minutes. The ALP activity of the osteoblast cells was tested using an ALP kit (Roche Applied Science). The ALP activity level in the control group which was treated with 10% DMSO was defined as 100%. Referring to FIG. 8A, imperatorin and bergapten both increased the ALP activity of the bone cells.

Example 14

Figure 8B:
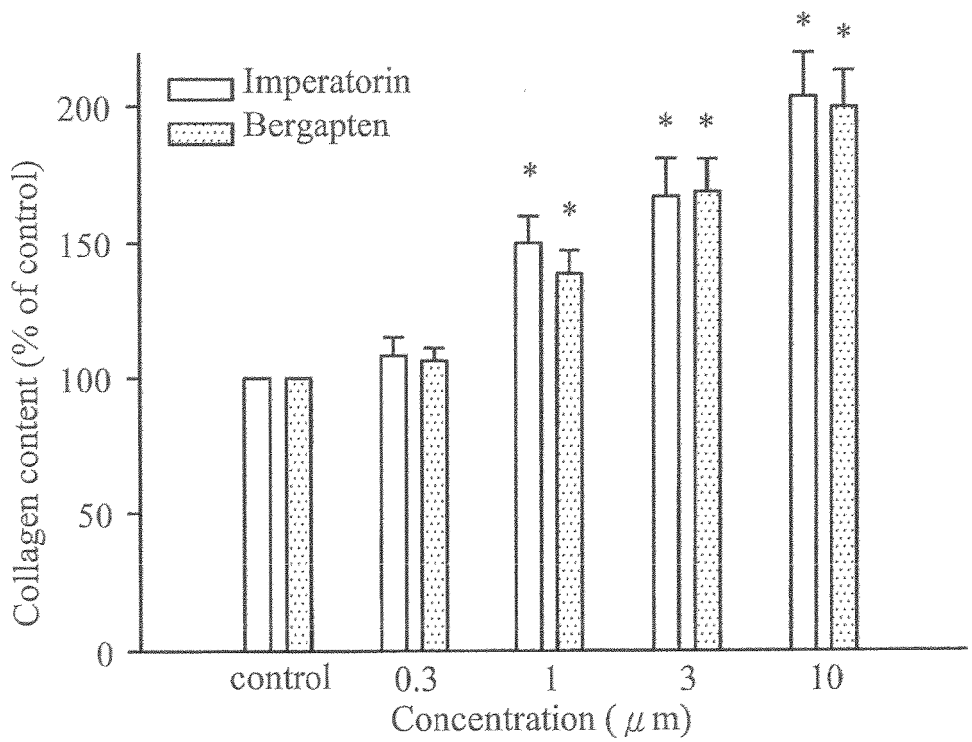
FIG. 8B shows the effect of imperatorin and bergapten on collagen secretion in the bone cells.

Effect of Imperatorin and Bergapten on Collagen Secretion in the Bone Cells Bone cells were treated with 0.3, 1, 3, and 10 μM of imperatorin and bergapten, respectively. After treatment, the cells were lysed in 6N HCl at 116° C. for 16 hrs, and dried in a vacuum. The resultant residue was dissolved in an equal volume of water, and then absorbance was measured at 550 mm. The collagen secretion in the control group which was treated with 0.1% DMSO was defined as 100%. Referring to FIG. 8B, imperatorin and bergapten both increased the collagen secretion in the bone cells

Example 15

Figure 8C:
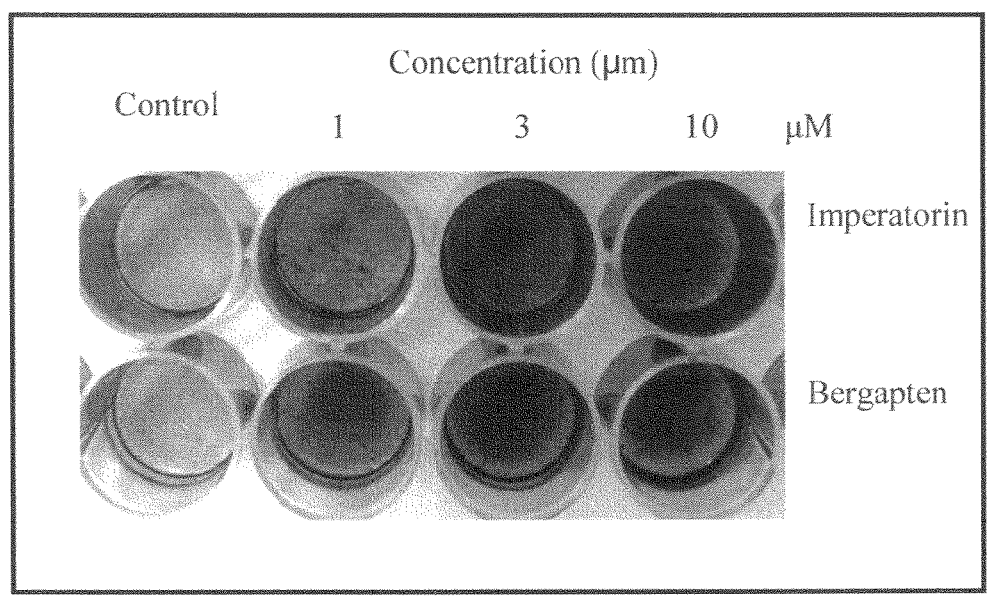
FIGS. 8C-8D show the effect of imperatorin and bergapten on bone mineralization.
Figure 8D:
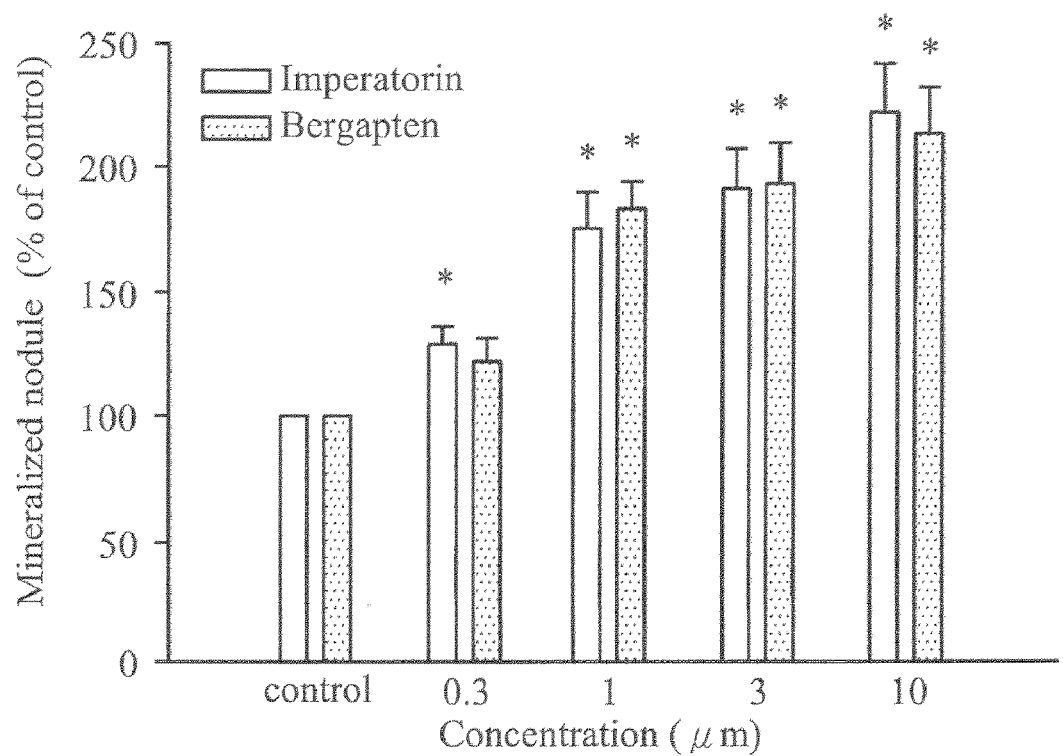

Effect of Imperatorin and Bergapten on the Mineralization in the Bone Cells Bone cells were cultured in 96-well Plate containing a differentiation medium (50 μg/ml vitamin C and 10 mM β-glycerophosphate) and treated with 0.3, 1, 3, and 10 μM of imperatorin and bergapten, respectively. The differentiation medium was refreshed every 3 days. 14 days after the cell culture, the bone cells were fixed with 75% ethanol for 30 minutes, and then treated with 40 mM Alizarin red-S at room temperature for 1 hr. After the addition of Alizarin red-S, 10% cetylpyridinium chloride was added, and then absorbance was measured at 550 mm. The mineralization level in the control group which was treated with 0.1% DMSO was defined as 100%. Referring to FIGS. 8C-8D, imperatorin and bergapten both increased the mineralization of bone cells.

Example 16

Effect of Imperatorin and Bergapten on the Expression of the BMP-2 Gene

Figure 9A:
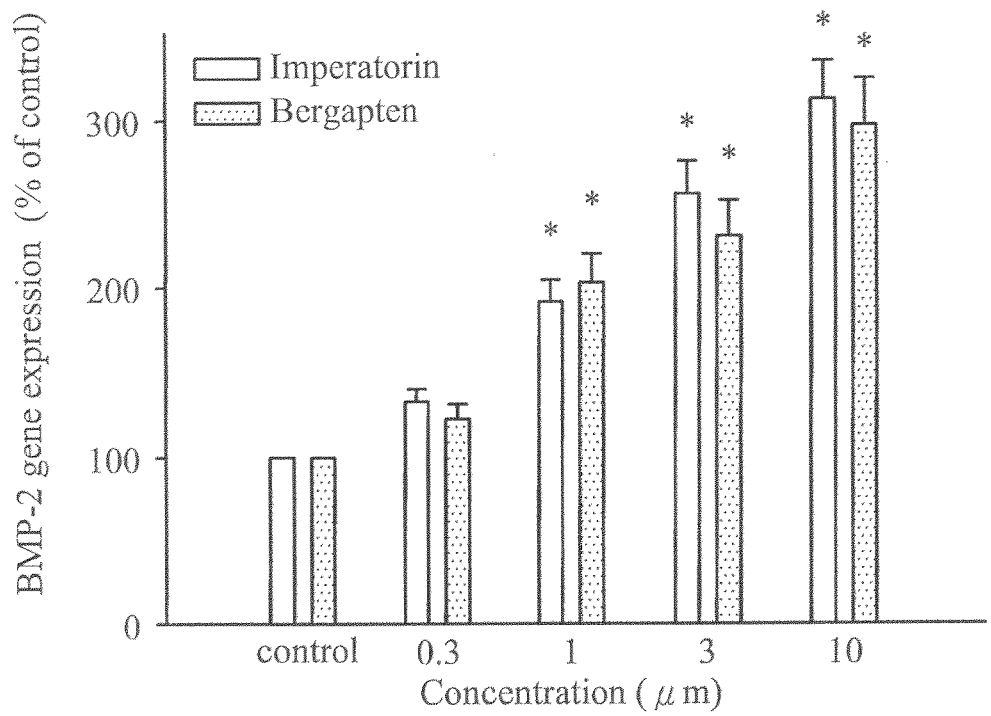
FIGS. 9A-9B show the effect of imperatorin and bergapten on BMP-2 gene expression.
Figure 9B:
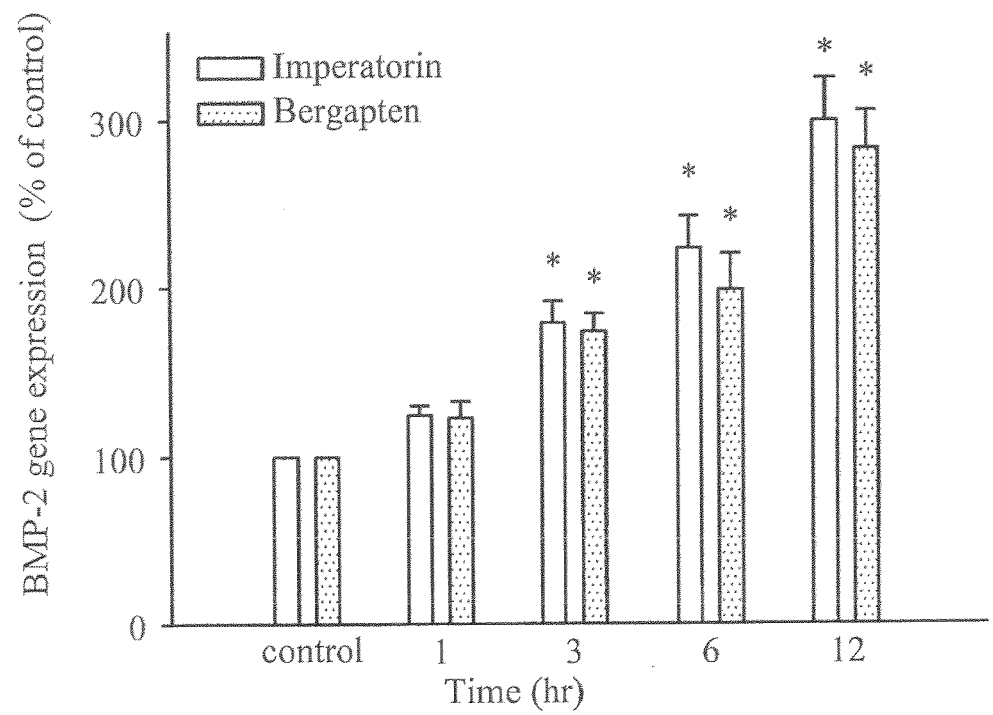

Bone cells were cultured in 6-well Plate and cultured with 0.3, 1, 3, and 10 μM of imperatorin and bergapten for 1, 3, 6, and 12 hrs, respectively. After treatment, the cells were lysed with TRIzol reagent at room temperature for 5 minutes, and then collected in a centrifuge tube. 0.5 ml of chloroform was added to the centrifuge tube. After the addition of chloroform, the centrifuge tube was well mixed, and centrifuged at 14000×g for 15 minutes at room temperature to obtain a supernatant. The supernatant was mixed with isopropanol (0.25 ml) and then centrifuged at 14000×g at room temperature for 15 minutes to obtain a precipitated RNA. RNA was washed with 75% alcohol, centrifuged at 14000×g for 10 minutes, and dried to give a RNA pellet. The RNA pellet was dissolved in diethyl pyrocarbonate (DEPC) solution and then quantitated by measurement of $OD_{260/280}$. BMP-2 gene expression (BMP-2 mRNA level) was detected by RT-PCR using Supperscript™ III reverstranscriptase and ABI Primer 700 (Applied Biosystems). The BMP-2 mRNA level in the control group which was treated with 0.1% DMSO was defined as 100%. Referring to FIG. 9A, BMP-2 mRNA level was increased according to the increase of the concentration of imperatorin or bergapten. Referring to FIG. 9B, BMP-2 mRNA level was increased according to the increase of the treatment time.

Example 17

Figure 9C:
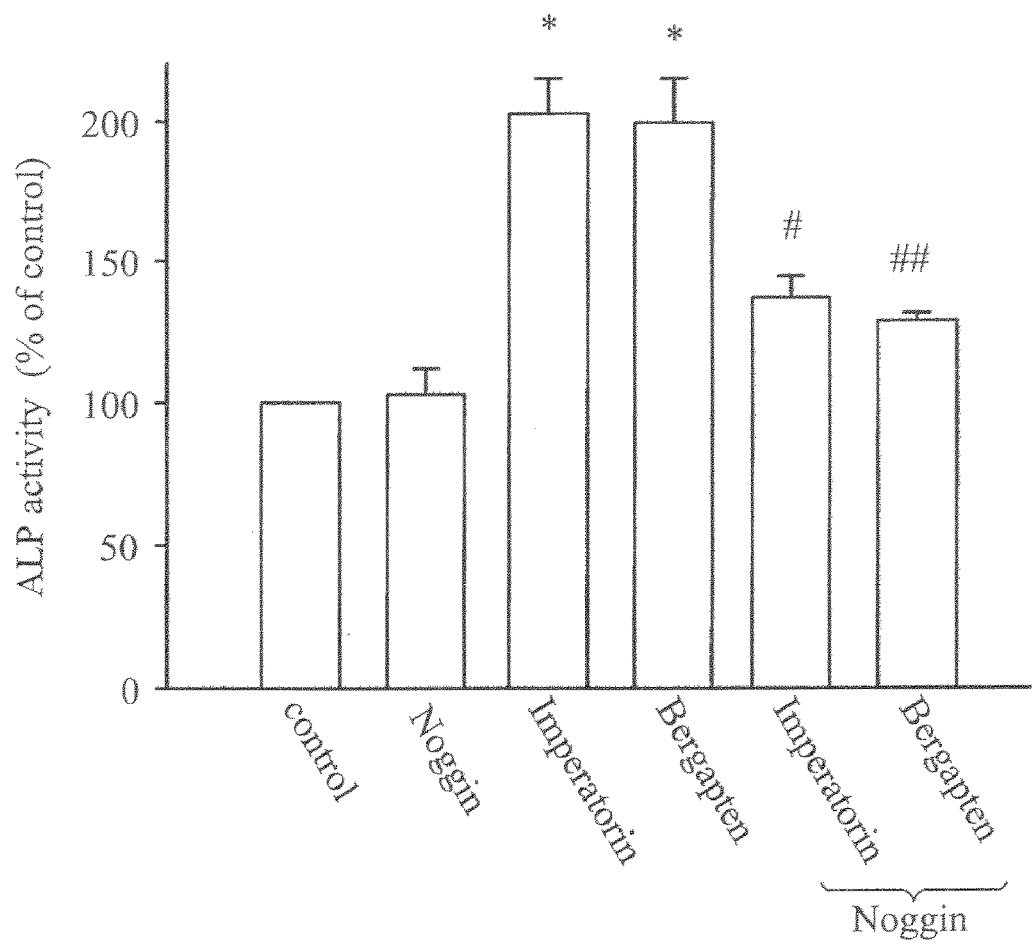
FIG. 9C shows the effect of imperatorin, bergapten, and noggin on BMP-2 gene expression.

Effect of Imperatorin, Bergapten and Noggin on the Expression of the BMP-2 Gene Bone cells were treated with (1) 10 μM imperatorin, (2) 10 μM bergapten, (3) 10 μM imperatorin+noggin, (4) 10 μM bergapten+noggin, and (5) 1 μg/ml noggin for 48 his, respectively. After treatment, the bone cells were lysed in 0.2% NT-40 solution, and then centrifuged at 1500×g for 5 minutes to obtain a supernatant. The supernatant was analyzed by ALP kit as described above to obtain the ALP activity. The ALP activity in the control group which was treated with 0.1% DMSO was defined as 100%. Referring to FIG. 9C, noggin suppressed the imperatorin or bergapten induced-ALP activity. Thus, it indicated that imperatorin or bergapten may increase BMP-2 expression to induce bone cells differentiation.

Example 18

Figure 10A:
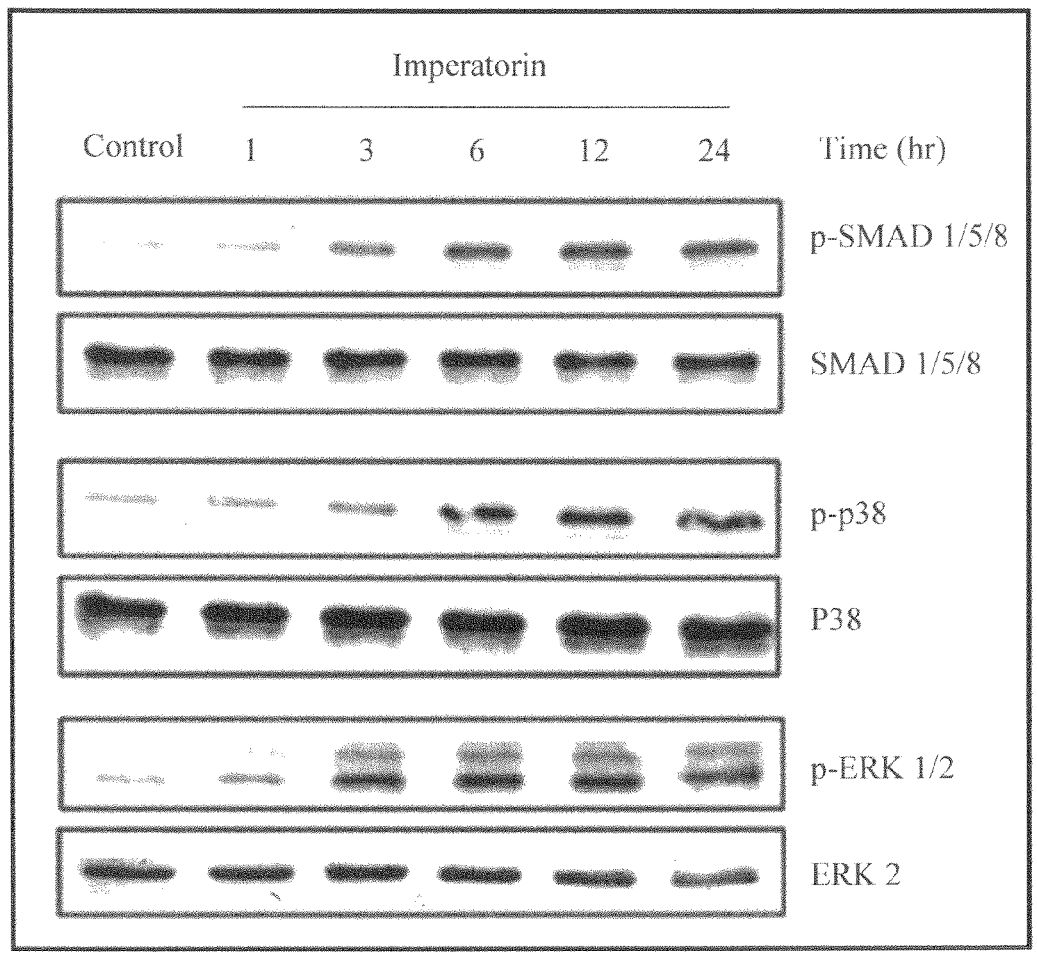
FIG. 10 shows the effect of imperatorin and bergapten on phosphorylation of SMADs, p38, and EPK protein in the bone cells.
Figure 10B:
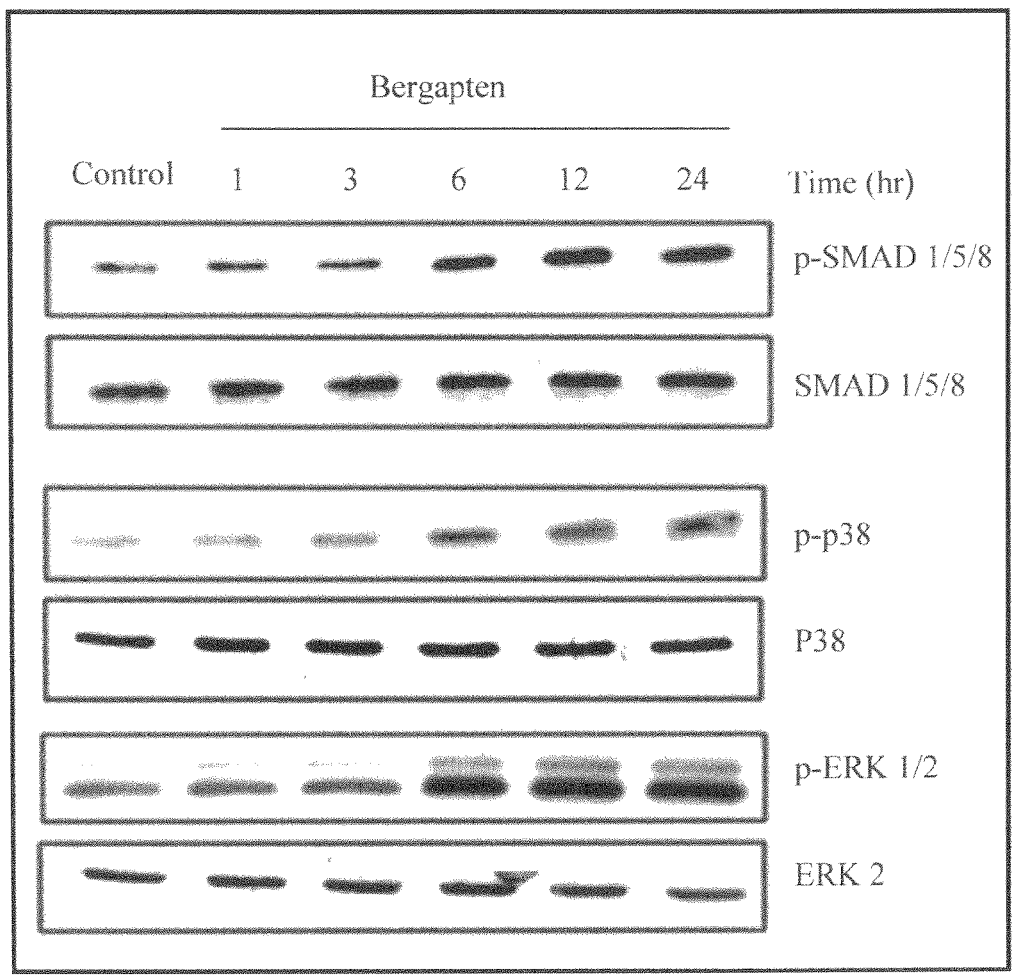

Effect of Imperatorin and Bergapten on Phosphorylation of SMADs, p38, and EPK Protein in the Bone Cells Bone cells was cultured in 6-well plate and treated with 10 μM of imperatorin and bergapten for 1, 3, 6, 12, and 24 hrs, respectively. After treatment, the culture medium was replaced with a lysis buffer containing 50 mM HEPES (PH 7.4), 150 mM NaCl, 4 mM EDTA, 10 mM $Na_4P_2O_7$, 100 mM NaF, 2 mM $Na_3VO_4$, 1% (v/v) Triton X-100, 0.25% (w/v) sodium deoxycholate, 50 mM 4-(2-aminoethyl)benzene sulfonylfluoride, 50 μg/ml leupeptin, and 20 μg/ml aprotinin, and then centrifuged at 13000 rpm for 15 minutes to obtain the protein pellets. 30 μg of proteins were dissolved in 5× Laemmli buffer, boiled at 95° C. for 5 minutes, and then subjected to SDS-PAGE gel (8%) electrophoresis. Proteins on the gel were then transferred to a PVDF membrane. The PVDF membrane was blocked in 4% BSA solution for 1 hour at room temperature. The blocked membrane was then incubated in PBST buffer (0.1% Tween-20) containing p-SMAD, p-ERK, or p38 primary antibody. Following incubation with primary antibody, the membrane was washed three times with PBST, and then incubated for 1 hr at room temperature with the secondary antibody, an anti-mouse or anti-goat IgG labeled with horseradish peroxidase. Following incubation with the secondary antibody, the membrane was washed three times with PBST, and detected by an enzyme-linked chemiluminescence using an ECL blotting substrate according to the manufacturer's instructions. Referring to FIG. 10, the phosphorylation of SMADs, p38, and EPK protein were induced by imperatorin and bergapten.

Example 19

Figure 11A:
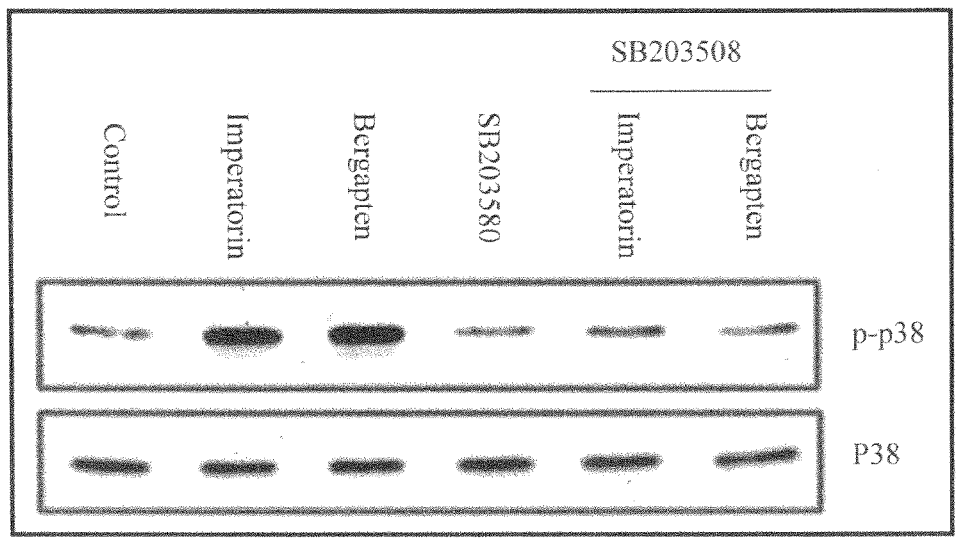
FIGS. 11A-11B show the effect of p38 and ERK inhibitor on phosphorylation of p38 and EPK protein in the bone cells.
Figure 11B:
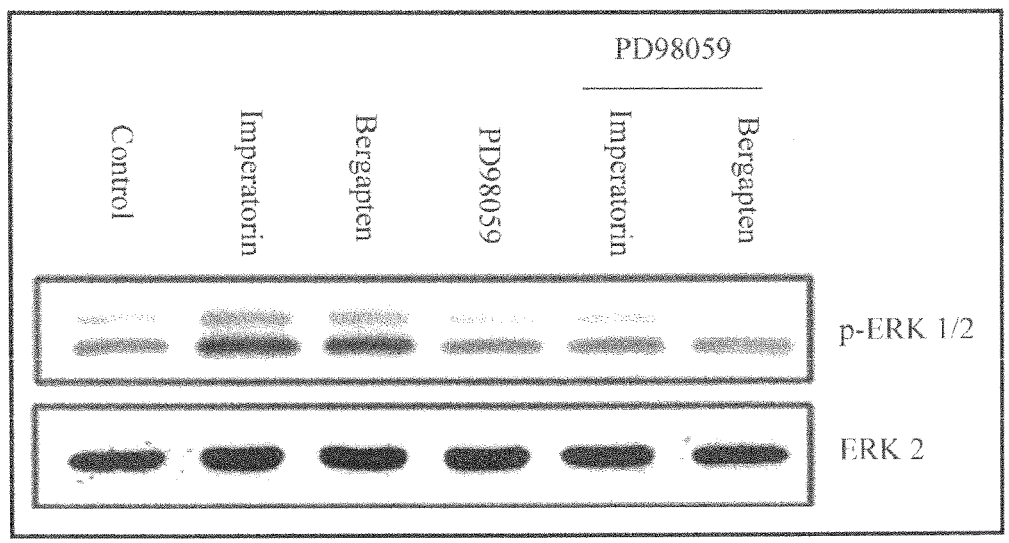

Effect of p38 Inhibitor (SB203580) and ERK Inhibitor (PD98059) on Phosphorylation of p38 and EPK Protein The same procedure carried out in Example 18 was repeated except that the bone cells were changed to be treated with p38 inhibitor (SB203580) and ERK inhibitor (PD98059) for 30 minutes, before the treatment of imperatorin and bergapten. In the control group, a non-phosphorylation p38 and non-phosphorylation EPK proteins were subjected to SDS-PAGE gel electrophoresis. Referring to FIGS. 11A-11B, p38 inhibitor (SB203580) and ERK inhibitor (PD98059) suppressed the imperatorin and bergapten induced-phosphorylation.

Example 20

Figure 11C:
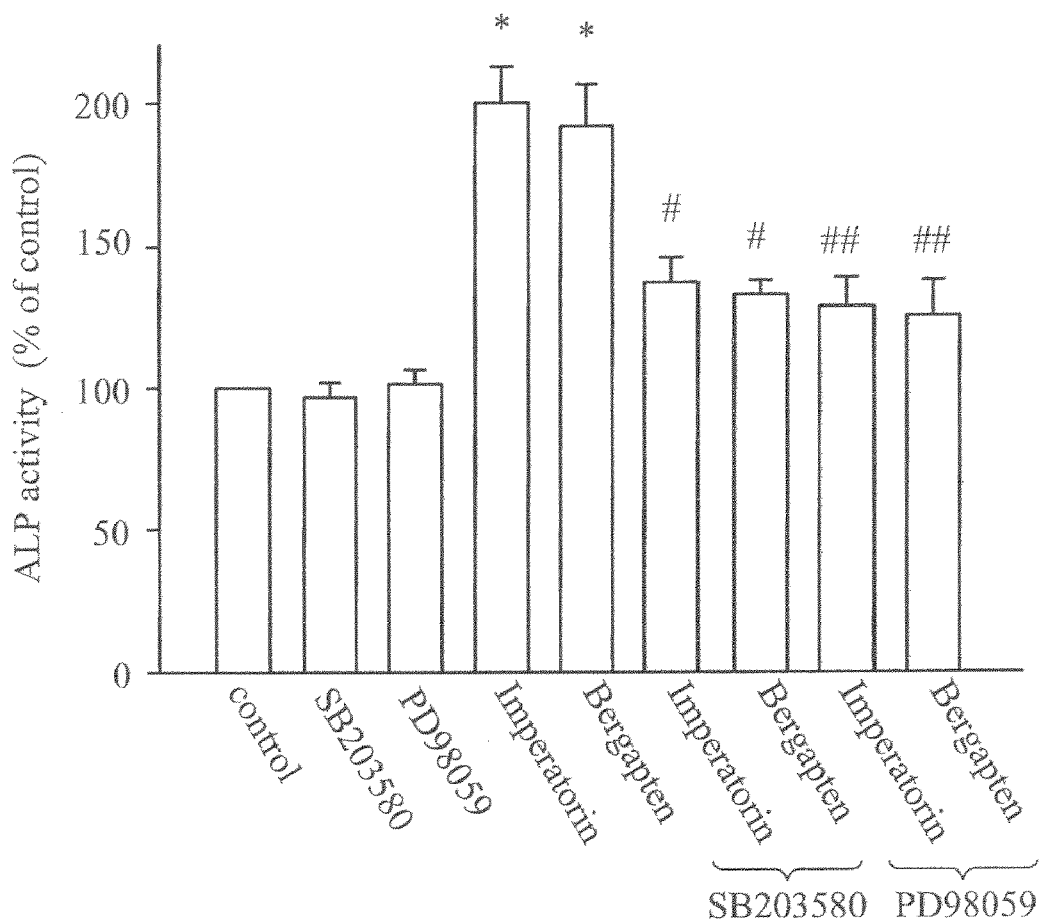
FIG. 11C shows the effect of p38 and ERK inhibitor on ALP activity in the bone cells.

Effect of p38 Inhibitor (SB203580) and ERK Inhibitor (PD98059) on ALP Activity in the Bone Cells Bone cells were cultured and treated with (1) 10 μM SB203580, (2) 10 μM PD98059, (3) 10 μM imperatori, (4) 10

μM bergapten, (5) 10 μM imperatorin+SB203580, (6) 10 μM bergapten+SB203580, (7) 10 μM imperatorin+PD98059 及(8) 10 μM bergapten+PD98059 for 48 hrs. After treatment, the bone cells were lysed in 0.2% NT-40 solution and centrifuged at 1500×g for 5 minutes. The supernatant was analyzed by an ALP kit such as described above to obtain the ALP activity. The ALP activity in the control group which was treated with 0.1% DMSO was defined as 100%. Referring to FIG. 11C, p38 inhibitor (SB203580) and ERK inhibitor (PD98059) suppressed the imperatorin and bergapten induced-ALP activity.

Example 21

Effect of Imperatorin and Bergapten on ALP Activity in p38 Mutant Cell (DN-p38) and ERK Mutant Cell (DN-ERK)

Figure 11D:
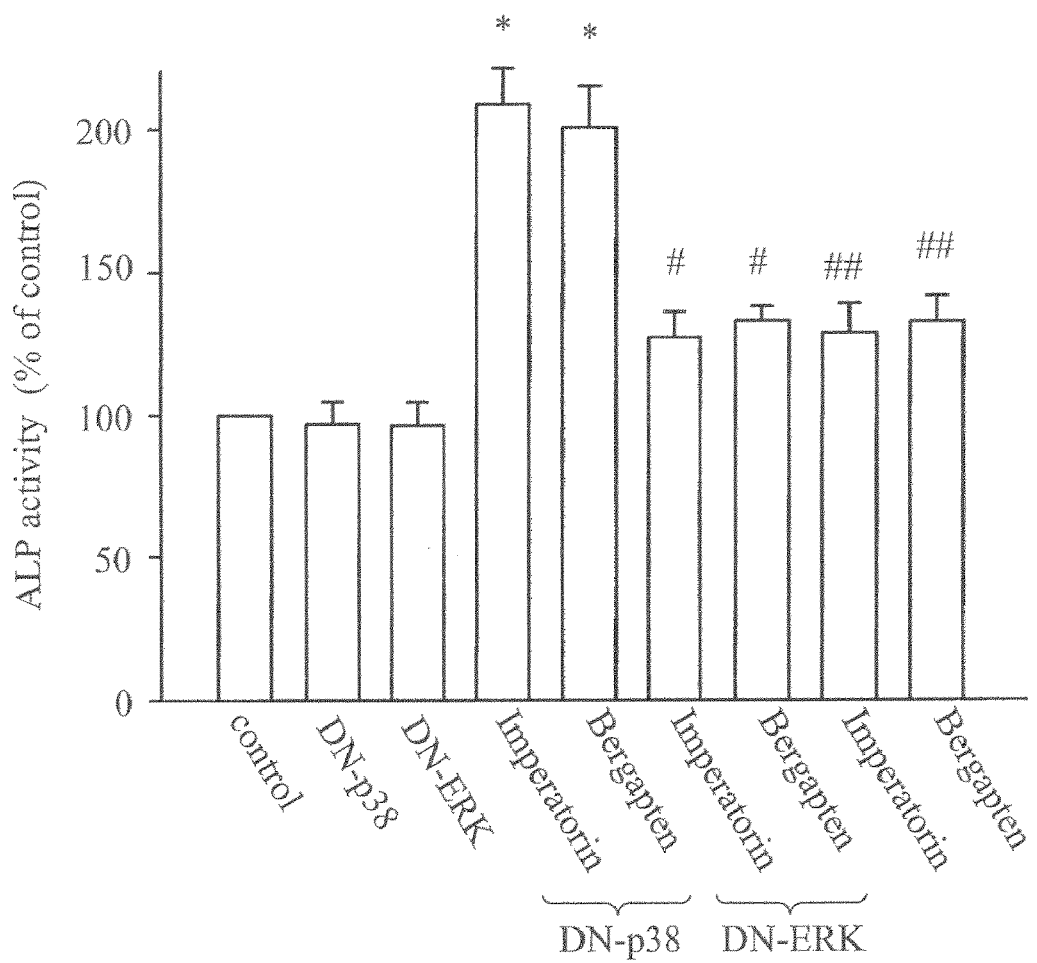
FIG. 11D shows of imperatorin and bergapten on ALP activity in p38 mutant cell (DN-p38) and ERK mutant cell (DN-ERK)

The same procedure carried out in Example 20 was repeated. The experiment group used alternative cells and treatment comprising: (1) DN-p38 cell, (2) DN-ERK cell, (3) DN-p38 cell+10 μM imperatorin, (4) DN-p38 cell+10 μM bergapten, (5) DN-ERK cell+10 μM imperatorin, (6) DN-ERK cell+10 μM bergapten, (7) normal bone cell+10 μM imperatorin, and (8) normal bone cell+10 μM bergapten. The ALP activity in the control group which was treated with 0.1% DMSO was defined as 100%. Referring to FIG. 11D, the ALP activity was not induced in p38 mutant cell (DN-p38) and ERK mutant cell (DN-ERK) by imperatorin and bergapten. Thus, the results indicate that the induction of the ALP activity relates to SMADs, p38, and EPK proteins.

Example 22

Animal Experiment

Figure 12:
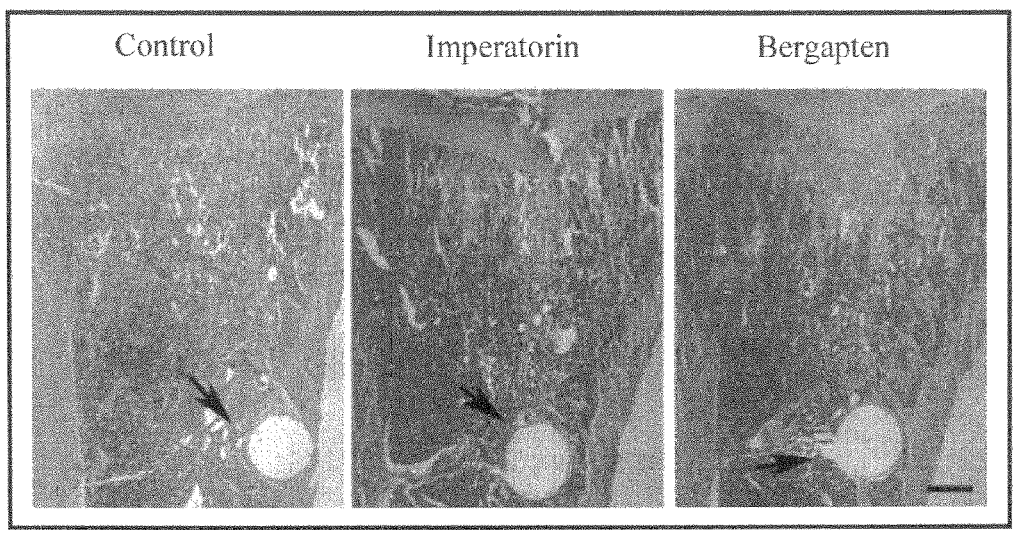
FIG. 12 is a photomicrograph showing the increase of the bone volume in tibia metaphysic by imperatorin and berapten.

Male Sprague-Dawley rats (weighing 78 to 90 grams, at three weeks of age) were anesthetized with 400 mg/ml of trichloroacetaldehyde monohydrate. A 22 G needle was sterilized and injected into the tibia of the rats. One day after the injection, the rats were administered with normal saline as the control, 30 μM imperatorin, and 30 μM bergapten every day for a week through the needle, respectively. Then, the rats were slaughtered after the last administration, and the tibias were immediately isolated after slaughtering and subject to BMD, BMC, and histochemical examination. Referring to FIG. 12, the bone volume of tibia metaphysis was increased by imperatorin and bergapten. The results of the BMD and BMC examinations are shown in Table 3.

TABLE 3

|  | Control | Imperatorin | Bergapten |
|---|---|---|---|
| BMD (g/cm$^3$) | 0.09 ± 0.001 | 0.101 ± 0.002* | 0.101 ± 0.002* |
| BMC (g) | 0.083 ± 0.002 | 0.107 ± 0.003* | 0.111 ± 0.003* |
| BV/TV (%) | 8.63 ± 0.2 | 17.6 ± 0.6* | 18.1 ± 0.4* |

BV/TV: bone volume/tissue volume
*p < 0.05: compared with sham group

The pharmaceutical composition can increase the weight of femur and tibia, bone mineral density, ALP activity, and synthesis of collagen to treat, reduce and ameliorate bone loss.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for ameliorating and/or treating bone loss, comprising administering to a subject an effective amount of a pharmaceutical composition comprising licorice, black soybean, Cnidi Fructus, and buckhorn, wherein a weight ratio of licorice, black soybean, Cnidi Fructus, and buckhorn is about 1-10:2-10:1-10:1-10.

2. The method as claimed in claim 1, wherein the ratio of licorice, black soybean, Cnidi Fructus, and buckhorn is about 2-4:4-6:1-3:1-3.

3. The method as claimed in claim 1, wherein the Cnidi Fructus comprises osthol.

4. The method as claimed in claim 1, wherein the Cnidi Fructus comprises imperatorin.

5. The method as claimed in claim 1, wherein the Cnidi Fructus comprises bergapten.

6. The method as claimed in claim 1, wherein the bone loss comprises osteoporosis or an osteoporotic fracture.

7. The method as claimed in claim 1, wherein the pharmaceutical composition increases bone mineral density (BMD) by at least 10.3%, increases bone mineral content (BMC) by at least 11.3% in a subject, and/or increases the alkaline phosphatase (ALP) activity by at least 90% in a bone cell.

8. The method as claimed in claim 1, wherein the pharmaceutical composition improves maximal load by at least 10.2%, improves ultimate loading by at least 13.2%, and/or improves Young's modulus by at least 10.1% in a bone tissue.

9. The method as claimed in claim 1, wherein the pharmaceutical composition improves ultimate stress by at least 34.8% in a bone tissue.

10. The method as claimed in claim 1, wherein the pharmaceutical is formed into a tablet, a capsule, a pellet, a powder, a solution, or a pill.

* * * * *